(12) United States Patent  
Tabor et al.

(10) Patent No.: US 11,951,007 B2  
(45) Date of Patent: Apr. 9, 2024

(54) DELIVERY SYSTEMS AND METHODS OF IMPLANTATION FOR PROSTHETIC HEART VALVES

(71) Applicant: MEDTRONIC, INC., Minneapolis, MN (US)

(72) Inventors: Charles Tabor, St. Cloud, MN (US); Timothy Ryan, Minnetrista, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 905 days.

(21) Appl. No.: 16/847,296

(22) Filed: Apr. 13, 2020

(65) Prior Publication Data

US 2020/0237541 A1    Jul. 30, 2020

Related U.S. Application Data

(63) Continuation of application No. 15/927,841, filed on Mar. 21, 2018, now Pat. No. 10,639,182, which is a
(Continued)

(51) Int. Cl.
*A61F 2/24* (2006.01)
*A61F 2/844* (2013.01)
(Continued)

(52) U.S. Cl.
CPC .......... *A61F 2/2436* (2013.01); *A61F 2/2412* (2013.01); *A61F 2/2418* (2013.01);
(Continued)

(58) Field of Classification Search
CPC .... A61F 2/2436; A61F 2/2412; A61F 2/2418; A61F 2/2439; A61F 2/844;
(Continued)

(56) References Cited

U.S. PATENT DOCUMENTS 3,334,629 A    8/1967    Cohn
3,409,013 A    11/1968   Berry
(Continued)

FOREIGN PATENT DOCUMENTS

CN    2007-100074433    1/2007
DE    3640745           6/1987
(Continued)

OTHER PUBLICATIONS

Opposition against European Patent No. 2 254 515 B1, Aug. 31, 2015.
(Continued)

*Primary Examiner* — Katherine M Rodjom
(74) *Attorney, Agent, or Firm* — Medler Ferro Woodhouse & Mills PLLC

(57) ABSTRACT

A delivery system for delivering an implantable stented device to a lumen of a patient, the delivery system including an elongated body having a proximal end and a distal end, a driver mechanism positioned at the proximal end of the elongated body, an elongated threaded rod located axially distal to the driver mechanism, and a sheath including an elongated tubular portion having a hollow interior portion with a first diameter that is sized for compression and retention of the implantable stented device in a compressed configuration for delivery to a body lumen.

22 Claims, 3 Drawing Sheets

Related U.S. Application Data continuation of application No. 15/183,906, filed on Jun. 16, 2016, now Pat. No. 9,925,079, which is a continuation of application No. 12/358,789, filed on Jan. 23, 2009, now Pat. No. 9,393,115.

(60) Provisional application No. 61/062,207, filed on Jan. 24, 2008.

(51) Int. Cl.
  *A61F 2/95* (2013.01)
  *A61F 2/966* (2013.01)

(52) U.S. Cl.
  CPC ............ *A61F 2/2439* (2013.01); *A61F 2/844* (2013.01); *A61F 2002/9505* (2013.01); *A61F 2002/9511* (2013.01); *A61F 2/9522* (2020.05); *A61F 2002/9665* (2013.01); *A61F 2250/0098* (2013.01)

(58) Field of Classification Search
  CPC ...... A61F 2002/9505; A61F 2002/9511; A61F 2002/9665
  See application file for complete search history.

(56) References Cited

U.S. PATENT DOCUMENTS

| | | |
|---|---|---|
| 3,540,431 A | 11/1970 | Mobin-Uddin |
| 3,587,115 A | 6/1971 | Shiley |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos |
| 4,291,420 A | 9/1981 | Reul |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,425,908 A | 1/1984 | Simon |
| 4,470,157 A | 9/1984 | Love |
| 4,501,030 A | 2/1985 | Lane |
| 4,506,394 A | 3/1985 | Bedard |
| 4,574,803 A | 3/1986 | Storz |
| 4,580,568 A | 4/1986 | Gianturco |
| 4,592,340 A | 6/1986 | Boyles |
| 4,610,688 A | 9/1986 | Silvestrini et al. |
| 4,612,011 A | 9/1986 | Kautzky |
| 4,647,283 A | 3/1987 | Carpentier et al. |
| 4,648,881 A | 3/1987 | Carpentier et al. |
| 4,655,771 A | 4/1987 | Wallsten |
| 4,662,885 A | 5/1987 | DiPisa, Jr. |
| 4,665,906 A | 5/1987 | Jervis |
| 4,681,908 A | 7/1987 | Broderick et al. |
| 4,710,192 A | 12/1987 | Liotta et al. |
| 4,733,665 A | 3/1988 | Palmaz |
| 4,777,951 A | 10/1988 | Cribier et al. |
| 4,787,899 A | 11/1988 | Lazarus |
| 4,796,629 A | 1/1989 | Grayzel |
| 4,797,901 A | 1/1989 | Goerne et al. |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,913,141 A | 4/1990 | Hillstead |
| 4,917,102 A | 4/1990 | Miller et al. |
| 4,922,905 A | 5/1990 | Strecker |
| 4,954,126 A | 9/1990 | Wallsten |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,061,273 A | 10/1991 | Yock |
| 5,085,635 A | 2/1992 | Cragg |
| 5,089,015 A | 2/1992 | Ross |
| 5,152,771 A | 10/1992 | Sabbaghian et al. |
| 5,161,547 A | 11/1992 | Tower |
| 5,163,953 A | 11/1992 | Vince |
| 5,167,628 A | 12/1992 | Boyles |
| 5,217,483 A | 6/1993 | Tower |
| 5,232,445 A | 8/1993 | Bonzel |
| 5,272,909 A | 12/1993 | Nguyen et al. |
| 5,295,958 A | 3/1994 | Shturman |
| 5,327,774 A | 7/1994 | Nguyen et al. |
| 5,332,402 A | 7/1994 | Teitelbaum |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,411,552 A | 5/1995 | Andersen et al. |
| 5,415,633 A | 5/1995 | Lazarus et al. |
| 5,431,676 A | 7/1995 | Dubrul et al. |
| 5,443,446 A | 8/1995 | Shturman |
| 5,449,384 A | 9/1995 | Johnson |
| 5,480,424 A | 1/1996 | Cox |
| 5,489,294 A | 2/1996 | McVenes et al. |
| 5,489,297 A | 2/1996 | Duran |
| 5,496,346 A | 3/1996 | Horzewski et al. |
| 5,500,014 A | 3/1996 | Quijano et al. |
| 5,507,767 A | 4/1996 | Maeda et al. |
| 5,545,209 A | 8/1996 | Roberts et al. |
| 5,545,211 A | 8/1996 | An et al. |
| 5,545,214 A | 8/1996 | Stevens |
| 5,554,185 A | 9/1996 | Block et al. |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,674,277 A | 10/1997 | Freitag |
| 5,693,083 A | 12/1997 | Baker et al. |
| 5,695,498 A | 12/1997 | Tower |
| 5,702,368 A | 12/1997 | Stevens et al. |
| 5,713,953 A | 2/1998 | Vallana et al. |
| 5,716,417 A | 2/1998 | Girard et al. |
| 5,746,709 A | 5/1998 | Rom et al. |
| 5,749,890 A | 5/1998 | Shaknovich |
| 5,766,151 A | 6/1998 | Valley et al. |
| 5,776,142 A | 7/1998 | Gunderson |
| 5,782,809 A | 7/1998 | Umeno et al. |
| 5,800,456 A | 9/1998 | Maeda et al. |
| 5,800,508 A | 9/1998 | Goicoechea et al. |
| 5,807,405 A | 9/1998 | Vanney et al. |
| 5,817,126 A | 10/1998 | Imran |
| 5,824,041 A | 10/1998 | Lenker |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |

(56) References Cited

U.S. PATENT DOCUMENTS

| | | |
|---|---|---|
| 5,824,064 A | 10/1998 | Taheri |
| 5,840,081 A | 11/1998 | Andersen et al. |
| 5,843,158 A | 12/1998 | Lenker et al. |
| 5,851,232 A | 12/1998 | Lois |
| 5,855,597 A | 1/1999 | Jayaraman |
| 5,855,601 A | 1/1999 | Bessler et al. |
| 5,860,996 A | 1/1999 | Urban et al. |
| 5,861,028 A | 1/1999 | Angell |
| 5,868,783 A | 2/1999 | Tower |
| 5,876,448 A | 3/1999 | Thompson et al. |
| 5,888,201 A | 3/1999 | Stinson et al. |
| 5,891,191 A | 4/1999 | Stinson |
| 5,906,619 A | 5/1999 | Olson et al. |
| 5,907,893 A | 6/1999 | Zadno-Azizi et al. |
| 5,913,842 A | 6/1999 | Boyd et al. |
| 5,925,063 A | 7/1999 | Khosravi |
| 5,944,738 A | 8/1999 | Amplatz et al. |
| 5,957,949 A | 9/1999 | Leonhardt et al. |
| 5,968,068 A | 10/1999 | Dehdashtian et al. |
| 5,984,957 A | 11/1999 | Laptewicz, Jr. et al. |
| 5,997,573 A | 12/1999 | Quijano et al. |
| 6,022,370 A | 2/2000 | Tower |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,042,607 A | 3/2000 | Williamson, IV |
| 6,051,104 A | 4/2000 | Jang |
| 6,059,809 A | 5/2000 | Amor et al. |
| 6,110,201 A | 8/2000 | Quijano et al. |
| 6,126,685 A | 10/2000 | Lenker et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,168,614 B1 | 1/2001 | Andersen et al. |
| 6,171,335 B1 | 1/2001 | Wheatley et al. |
| 6,200,336 B1 | 3/2001 | Pavcnik et al. |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,248,116 B1 | 6/2001 | Chevilon |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,299,637 B1 | 10/2001 | Shaolia et al. |
| 6,302,906 B1 | 10/2001 | Goicoechea et al. |
| 6,309,382 B1 | 10/2001 | Garrison et al. |
| 6,309,417 B1 | 10/2001 | Spence et al. |
| 6,338,735 B1 | 1/2002 | Stevens |
| 6,346,118 B1 | 2/2002 | Baker et al. |
| 6,348,063 B1 | 2/2002 | Yassour et al. |
| 6,350,277 B1 | 2/2002 | Kocur |
| 6,352,708 B1 | 3/2002 | Duran et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,482,228 B1 | 11/2002 | Norred |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,585,758 B1 | 7/2003 | Chouinard et al. |
| 6,592,546 B1 | 7/2003 | Barbut et al. |
| 6,605,112 B1 | 8/2003 | Moll et al. |
| 6,613,077 B2 | 9/2003 | Gilligan et al. |
| 6,622,604 B1 | 9/2003 | Chouinard et al. |
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Liddicoat et al. |
| 6,786,925 B1 | 9/2004 | Buchanan et al. |
| 6,790,229 B1 | 9/2004 | Berreklouw |
| 6,790,230 B2 | 9/2004 | Beyersdorf et al. |
| 6,792,979 B2 | 9/2004 | Konya et al. |
| 6,797,002 B2 | 9/2004 | Spence et al. |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof |
| 6,846,325 B2 | 1/2005 | Liddicoat |
| 6,866,650 B2 | 3/2005 | Stevens |
| 6,866,669 B2 | 3/2005 | Buzzard |
| 6,872,223 B2 | 3/2005 | Roberts |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Streeter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,974,474 B2 | 12/2005 | Pavcnik et al. |
| 6,974,476 B2 | 12/2005 | McGuckin et al. |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,101,396 B2 | 9/2006 | Artof et al. |
| 7,105,016 B2 | 9/2006 | Shui et al. |
| 7,115,141 B2 | 10/2006 | Menz et al. |
| 7,128,759 B2 | 10/2006 | Osborne et al. |

(56) References Cited

U.S. PATENT DOCUMENTS

| | | |
|---|---|---|
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,252,682 B2 | 8/2007 | Seguin |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin |
| 7,335,218 B2 | 2/2008 | Wilson et al. |
| 7,338,520 B2 | 3/2008 | Bailey et al. |
| 7,374,571 B2 | 5/2008 | Pease et al. |
| 7,377,938 B2 | 5/2008 | Sarac et al. |
| 7,381,218 B2 | 6/2008 | Schreck |
| 7,384,411 B1 | 6/2008 | Condado |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,544,206 B2 | 6/2009 | Cohn et al. |
| 7,547,322 B2 | 6/2009 | Sarac et al. |
| 7,556,646 B2 | 7/2009 | Yang et al. |
| 7,682,390 B2 | 3/2010 | Seguin |
| 7,722,666 B2 | 5/2010 | Lafontaine |
| 7,780,726 B2 | 8/2010 | Seguin |
| 7,803,177 B2 | 9/2010 | Hartley et al. |
| 7,806,919 B2 | 10/2010 | Bloom et al. |
| 7,959,666 B2 | 6/2011 | Salahieh et al. |
| 7,959,672 B2 | 6/2011 | Salahieh et al. |
| 7,972,378 B2 | 7/2011 | Tabor et al. |
| 8,252,052 B2 | 8/2012 | Salahieh et al. |
| 8,343,213 B2 | 1/2013 | Salahieh et al. |
| 8,603,160 B2 | 12/2013 | Salahieh et al. |
| 8,673,000 B2 | 3/2014 | Tabor et al. |
| 8,828,078 B2 | 9/2014 | Salahieh et al. |
| 8,840,663 B2 | 9/2014 | Salahieh et al. |
| 9,132,024 B2 | 9/2015 | Brinser |
| 9,339,382 B2 | 5/2016 | Tabor et al. |
| 9,393,115 B2 | 7/2016 | Tabor et al. |
| 2001/0001314 A1 | 5/2001 | Davison et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2002/0010508 A1 | 1/2002 | Chobotov |
| 2002/0029014 A1 | 3/2002 | Jayaraman |
| 2002/0032480 A1 | 3/2002 | Spence et al. |
| 2002/0032481 A1 | 3/2002 | Gabbay |
| 2002/0035396 A1 | 3/2002 | Heath |
| 2002/0042650 A1 | 4/2002 | Vardi et al. |
| 2002/0052651 A1 | 5/2002 | Myers et al. |
| 2002/0058995 A1 | 5/2002 | Stevens |
| 2002/0072789 A1 | 6/2002 | Hackett et al. |
| 2002/0095209 A1 | 7/2002 | Zadno-Azizi et al. |
| 2002/0099439 A1 | 7/2002 | Schwartz et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0133183 A1 | 9/2002 | Lentz et al. |
| 2002/0138138 A1 | 9/2002 | Yang |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0036791 A1 | 2/2003 | Bonhoeffer et al. |
| 2003/0040771 A1 | 2/2003 | Hyodoh et al. |
| 2003/0040772 A1 | 2/2003 | Hyodoh et al. |
| 2003/0040792 A1 | 2/2003 | Gabbay |
| 2003/0050684 A1 | 3/2003 | Abrams et al. |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0125795 A1 | 7/2003 | Pavcnik et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0181850 A1 | 9/2003 | Diamond et al. |
| 2003/0191519 A1 | 10/2003 | Lombardi et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0212410 A1 | 11/2003 | Stenzel et al. |
| 2003/0212454 A1 | 11/2003 | Scott et al. |
| 2003/0225445 A1 | 12/2003 | Derus et al. |
| 2003/0233140 A1 | 12/2003 | Hartley et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0073289 A1* | 4/2004 | Hartley ............... A61F 2/95 623/1.13 |
| 2004/0082904 A1 | 4/2004 | Houde et al. |
| 2004/0082989 A1 | 4/2004 | Cook et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093060 A1 | 5/2004 | Sequin et al. |
| 2004/0093063 A1* | 5/2004 | Wright ............... A61F 2/95 623/1.12 |
| 2004/0093075 A1 | 5/2004 | Kuehn |
| 2004/0097788 A1 | 5/2004 | Mourles et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson |
| 2004/0167620 A1 | 8/2004 | Ortiz |
| 2004/0186563 A1 | 9/2004 | Iobbi |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0220655 A1 | 11/2004 | Swanson et al. |
| 2004/0225353 A1 | 11/2004 | McGuckin, Jr. |
| 2004/0225354 A1 | 11/2004 | Allen |
| 2004/0254636 A1 | 12/2004 | Flagle et al. |
| 2004/0260389 A1 | 12/2004 | Case et al. |

(56) References Cited

U.S. PATENT DOCUMENTS

| | | |
|---|---|---|
| 2004/0260394 A1 | 12/2004 | Douk et al. |
| 2004/0267357 A1 | 12/2004 | Allen et al. |
| 2005/0010246 A1 | 1/2005 | Streeter |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075727 A1 | 4/2005 | Wheatley |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119688 A1 | 6/2005 | Berheim |
| 2005/0131438 A1 | 6/2005 | Cohn |
| 2005/0137686 A1 | 6/2005 | Salahieh |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137692 A1 | 6/2005 | Haug |
| 2005/0137695 A1 | 6/2005 | Salahieh |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh |
| 2005/0143807 A1 | 6/2005 | Pavcnik et al. |
| 2005/0143809 A1* | 6/2005 | Salahieh ............ A61F 2/2418 623/2.11 |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0187616 A1 | 8/2005 | Realyvasquez |
| 2005/0197695 A1 | 9/2005 | Stacchino et al. |
| 2005/0203549 A1 | 9/2005 | Realyvasquez |
| 2005/0203605 A1 | 9/2005 | Dolan |
| 2005/0203618 A1 | 9/2005 | Sharkawy |
| 2005/0222674 A1* | 10/2005 | Paine .................. A61F 2/2439 623/2.14 |
| 2005/0228495 A1 | 10/2005 | Macoviak |
| 2005/0234546 A1 | 10/2005 | Nugent |
| 2005/0240200 A1 | 10/2005 | Bergheim |
| 2005/0240263 A1 | 10/2005 | Fogarty et al. |
| 2005/0261759 A1 | 11/2005 | Lambrecht et al. |
| 2005/0283231 A1 | 12/2005 | Haug et al. |
| 2005/0283962 A1 | 12/2005 | Boudjemline |
| 2006/0004439 A1 | 1/2006 | Spenser et al. |
| 2006/0004469 A1 | 1/2006 | Sokel |
| 2006/0009841 A1 | 1/2006 | McGuckin et al. |
| 2006/0052867 A1 | 3/2006 | Revuelta et al. |
| 2006/0058775 A1 | 3/2006 | Stevens et al. |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0167474 A1 | 7/2006 | Bloom et al. |
| 2006/0173524 A1 | 8/2006 | Salahieh et al. |
| 2006/0178740 A1 | 8/2006 | Stacchino et al. |
| 2006/0195134 A1 | 8/2006 | Crittenden |
| 2006/0206192 A1 | 9/2006 | Tower et al. |
| 2006/0206202 A1 | 9/2006 | Bonhoefer et al. |
| 2006/0212111 A1 | 9/2006 | Case et al. |
| 2006/0224227 A1 | 10/2006 | Chobotov |
| 2006/0235509 A1 | 10/2006 | Lafontaine |
| 2006/0247763 A1 | 11/2006 | Slater |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265045 A1 | 11/2006 | Shiu et al. |
| 2006/0265056 A1 | 11/2006 | Nguyen et al. |
| 2006/0271166 A1 | 11/2006 | Thill et al. |
| 2006/0271175 A1 | 11/2006 | Woolfson et al. |
| 2006/0276813 A1* | 12/2006 | Greenberg ............ A61F 2/2418 606/158 |
| 2006/0276874 A1 | 12/2006 | Wilson et al. |
| 2006/0276882 A1 | 12/2006 | Case et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Raffiee et al. |
| 2007/0016281 A1 | 1/2007 | Melsheimer |
| 2007/0016286 A1 | 1/2007 | Case et al. |
| 2007/0027518 A1 | 2/2007 | Herrmann et al. |
| 2007/0027533 A1 | 2/2007 | Douk |
| 2007/0038295 A1 | 2/2007 | Case et al. |
| 2007/0043431 A1 | 2/2007 | Melsheimer |
| 2007/0043435 A1 | 2/2007 | Seguin et al. |
| 2007/0051377 A1 | 3/2007 | Douk et al. |
| 2007/0073392 A1 | 3/2007 | Heyninck-Janitz |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100435 A1 | 5/2007 | Case et al. |
| 2007/0100439 A1 | 5/2007 | Cangialosi |
| 2007/0100440 A1 | 5/2007 | Figulla |
| 2007/0100449 A1 | 5/2007 | O'Neil et al. |
| 2007/0112415 A1 | 5/2007 | Bartlett |
| 2007/0112422 A1 | 5/2007 | Dehdashtian |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0203503 A1 | 8/2007 | Salahieh et al. |
| 2007/0208550 A1 | 9/2007 | Cao et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Marchand et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239271 A1 | 10/2007 | Nguyen |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0288000 A1 | 12/2007 | Bonan |
| 2007/0288087 A1 | 12/2007 | Fearnot et al. |
| 2008/0004696 A1 | 1/2008 | Vesely |

(56) References Cited

U.S. PATENT DOCUMENTS

| | | |
|---|---|---|
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan |
| 2008/0065001 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0077234 A1 | 3/2008 | Styrc |
| 2008/0082165 A1 | 4/2008 | Wilson et al. |
| 2008/0082166 A1 | 4/2008 | Styrc et al. |
| 2008/0133003 A1 | 6/2008 | Seguin et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichow et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188921 A1 * | 8/2008 | Yamasaki ............ A61B 5/062 623/1.13 |
| 2008/0188928 A1 | 8/2008 | Salahieh et al. |
| 2008/0215143 A1 | 9/2008 | Seguin et al. |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0262592 A1 | 10/2008 | Jordan et al. |
| 2008/0262593 A1 | 10/2008 | Ryan et al. |
| 2008/0269878 A1 | 10/2008 | Iobbi |
| 2008/0275540 A1 | 11/2008 | Wen |
| 2009/0005863 A1 | 1/2009 | Goetz et al. |
| 2009/0012600 A1 | 1/2009 | Styrc et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0082858 A1 | 3/2009 | Nugent et al. |
| 2009/0085900 A1 | 4/2009 | Weiner |
| 2009/0099653 A1 | 4/2009 | Suri et al. |
| 2009/0138079 A1 | 5/2009 | Tuval et al. |
| 2009/0164004 A1 | 6/2009 | Cohn |
| 2009/0164006 A1 | 6/2009 | Seguin et al. |
| 2009/0171431 A1 | 7/2009 | Swanson et al. |
| 2009/0171447 A1 | 7/2009 | VonSeggesser et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198316 A1 | 8/2009 | Laske et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0222082 A1 | 9/2009 | Lock et al. |
| 2009/0234443 A1 | 9/2009 | Ottma et al. |
| 2009/0240264 A1 | 9/2009 | Tuval et al. |
| 2009/0240320 A1 | 9/2009 | Tuval |
| 2009/0287296 A1 | 11/2009 | Manasse |
| 2010/0004740 A1 | 1/2010 | Seguin et al. |
| 2010/0030328 A1 | 2/2010 | Seguin et al. |
| 2010/0036479 A1 | 2/2010 | Hill et al. |
| 2010/0036485 A1 | 2/2010 | Seguin |
| 2010/0069852 A1 | 3/2010 | Kelley |
| 2010/0094411 A1 | 4/2010 | Tuval et al. |
| 2010/0100167 A1 | 4/2010 | Bortlein et al. |
| 2010/0131054 A1 | 5/2010 | Tuval et al. |
| 2010/0137979 A1 | 6/2010 | Tuval et al. |
| 2010/0145439 A1 | 6/2010 | Seguin et al. |
| 2010/0152840 A1 | 6/2010 | Seguin et al. |
| 2010/0161045 A1 | 6/2010 | Righini |
| 2010/0198346 A1 | 8/2010 | Keogh et al. |
| 2010/0234940 A1 | 9/2010 | Dolan |
| 2010/0249923 A1 | 9/2010 | Alkhatib et al. |
| 2010/0256723 A1 | 10/2010 | Murray |
| 2010/0262157 A1 | 10/2010 | Silver et al. |
| 2012/0172982 A1 | 7/2012 | Stacchino et al. |
| 2014/0155997 A1 | 6/2014 | Braido |

FOREIGN PATENT DOCUMENTS

| | | |
|---|---|---|
| DE | 195 32 846 | 3/1997 |
| DE | 195 46 692 A1 | 6/1997 |
| DE | 195 46 692 C2 | 6/1997 |
| DE | 198 57 887 A1 | 7/2000 |
| DE | 199 07 646 | 8/2000 |
| DE | 100 10 074 | 10/2001 |
| DE | 100 49 812 | 4/2002 |
| DE | 100 49 813 | 4/2002 |
| DE | 100 49 815 | 4/2002 |
| EP | 1057460 A1 | 6/2000 |
| EP | 1255510 | 11/2002 |
| EP | 1440673 A1 | 7/2004 |
| EP | 1469797 | 11/2005 |
| FR | 2788217 | 12/1999 |
| FR | 2815844 | 5/2000 |
| GB | 2056023 | 3/1981 |
| GB | 2433700 | 12/2007 |
| SU | 1271508 | 11/1986 |
| WO | 95/29640 | 11/1995 |
| WO | 00/44313 | 8/2000 |
| WO | 00/47136 | 8/2000 |
| WO | 01/35870 | 5/2001 |
| WO | 01/49213 | 7/2001 |
| WO | 01/54625 | 8/2001 |
| WO | 01/62189 | 8/2001 |
| WO | 01/64137 | 9/2001 |
| WO | 02/22054 | 3/2002 |
| WO | 02/36048 | 5/2002 |
| WO | 03/003943 | 1/2003 |
| WO | 03/003949 | 1/2003 |
| WO | 03/011195 | 2/2003 |
| WO | 04/019825 | 3/2004 |
| WO | 04/089250 | 10/2004 |
| WO | 05/004753 | 1/2005 |
| WO | 05/046528 | 5/2005 |
| WO | 2005/062980 A2 | 7/2005 |
| WO | 2005/079151 A2 | 9/2005 |
| WO | 06/026371 | 3/2006 |
| WO | 2007/022496 A2 | 2/2007 |
| WO | 08/047354 | 4/2008 |
| WO | 08/138584 | 11/2008 |
| WO | 08/150529 | 12/2008 |
| WO | 09/002548 | 12/2008 |
| WO | 09/029199 | 3/2009 |
| WO | 09/042196 | 4/2009 |
| WO | 09/045338 | 4/2009 |
| WO | 09/061389 | 5/2009 |
| WO | 09/091509 | 7/2009 |
| WO | 09/111241 | 9/2009 |

OTHER PUBLICATIONS

Andersen, H.R. et al, "Transluminal implantation of artificial heart valves. Description of a new expandable aortic valve and initial results with imglantation by catheter technigue in closed chest gigs." Euro. Heart J. (1992) 13:704-708.

Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.

(56) References Cited

OTHER PUBLICATIONS

Bailey, "Percutaneous Expandable Prosthetic Valves," In: Topol EJ, ed. Textbook of Interventional Cardiology. vol. II. Second edition. WB Saunders, Philadelphia, 1994:1268-1276.
Block, et al., "Percutaneous Approaches to Valvular Heart Disease," Current Cardiology Reports, vol. 7 (2005) pp. 108-113.
Bonhoeffer, et al, "Percutaneous Insertion of the Pulmonary Valve," Journal of the American College of Cardiology (United States), May 15, 2002, pp. 1664-9.
Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-5.
Bonhoeffer, et al, "Transcatheter Implantation of a Bovine Valve in Pulmonary Position: A Lamb Study," Circulation (United States), Aug. 15, 2000, pp. 813-6.
Boudjemline, et al, "Images in Cardiovascular Medicine. Percutaneous Aortic Valve Replacement in Animals," Circulation (United States), Mar. 16, 2004, 109, p. e161.
Boudjemline, et al, "Is Percutaneous Implantation of a Bovine Venous Valve in the Inferior Vena Cava a Reliable Technique to Treat Chronic Venous Insufficiency Syndrome?" Medical Science Monito—International Medical Journal of Experimental and Clinical Research (Poland), Mar. 2004, pp. BR61-6.
Boudjemline, et al, "Off-pump Replacement of the Pulmonary Valve in Large Right Ventricular Outflow Tracts: A Hybrid Aggroach," Journal of Thoracic and Cardiovascular Surgery (United States), Apr. 2005, pp. 831-7.
Boudjemline, et al, "Percutaneous Aortic Valve Replacement: Will We Get There?" Heart (British Cardiac Society) (England), Dec. 2001, pp. 705-6.
Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-6.
Boudjemline, et al, "Percutaneous Implantation of a Biological Valve in Aortic Position: Preliminary Results in a Sheep Study," European Heart Journal 22, Sep. 2001, p. 630.
Boudjemline, et al, "Percutaneous Implantation of a Valve in the Descending Aorta in Lambs," European Heart Journal (England), Jul. 2002, pp. 1045-9.
Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-7.
Boudjemline, et al, "Percutaneous Valve Insertion: A New Approach," Journal of Thoracic and Cardiovascular Surgery (United States), Mar. 2003, pp3. 741-2.
Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.
Boudjemline, et al, "Steps Toward Percutaneous Aortic Valve Replacement," Circulation (United States), Feb. 12, 2002, pp. 775-8.
Boudjemline, et al, "The Percutaneous Implantable Heart Valve," Progress in Pediatric Cardiology (Ireland), 2001, pp. 89-93.
Boudjemline, et al, "Transcatheter Reconstruction of the Right Heart," Cardiology in the Young (England), Jun. 2003, pp. 308-11.
Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.
Cribier, A. et al, "Percutaneous Transcatheter Implantation of an Aortic Valve Prosthesis for Calcific Aortic Stenosis: First Human Case Description," Circulation (2002) 3006-3008.
Davidson et al., "Percutaneous therapies for valvular heart disease," Cardiovascular Pathology 15 (2006) 123-129.
European Patent Office Communication in Application No. 09704087.7-2320, dated Nov. 30, 2012, 5 pages.
Hanzel, et al., "Complications of percutaneous aortic valve replacement: experience with the Criber-Edwards™ percutaneous heart valve," EuroIntervention Supplements (2006), 1 (Supplement A) A3-A8.
Huber, et al., "Do Valved Stents Compromise Coronary Flow?" Eur. J. Cardiothorac. Surg. 2004;25:754-759.
Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.
Khambadkone, et al, "Percutaneous Implantation of Pulmonary Valves," Expert Review of Cardiovascular Therapy (England), Nov. 2003, pp. 541-548.
Khambadkone, et al, "Percutaneous Pulmonary Valve Implantation: Early and Medium Term Results," Circulation 108 (17 Supplement), Oct. 28, 2003, p. IV-375.
Khambadkone, et al, "Percutaneous Pulmonary Valve Implantation: Impact of Morphology on Case Selection," Circulation 108 (17 Supplement), Oct. 28, 2003, p. IV-642-IV-643.
Lutter, et al, "Percutaneous Aortic Valve Replacement: An Experimental Study. I. Studies on Implantation," The Journal of Thoracic and Cardiovascular Surgery, Apr. 2002, pp. 768-776.
Lutter, et al, "Percutaneous Valve Replacement: Current State and Future Prospects," Annals of Thoracic Surgery (Netherlands), Dec. 2004, pp. 2199-2206.
Ma, Ling, et al., "Double-crowned valved stents for off-pump mitral valve replacement," European Journal of Cardio Thoracic Surgery, 28:194-198, 2005.
Medtech Insight, "New Frontiers in Heart Valve Disease," vol. 7, No. 8 (2005).
Palacios, "Percutaneous Valve Replacement and Repair, Fiction or Reality?" Journal of American College of Cardiology, vol. 44, No. 8 (2004) pp. 1662-1663.
Pelton et al., "Medical Uses of Nitinol," Materials Science Forum vols. 327-328, pp. 63-70 (2000).
Ruiz, "Transcathether Aortic Valve Implantation and Mitral Valve Repair: State of the Art," Pediatric Cardiology, vol. 26, No. 3 (2005).
Saliba, et al., "Treatment of Obstructions of Prosthetic Conduits by Percutaneous Implantation of Stents," Archives des Maldies du Coeur et des Vaisseaux (France), 1999, pp. 591-596.
Webb, et al., "Percutaneous Aortic Valve Implantation Retrograde from the Femoral Artery," Circulation (2006), 113;842-850.
Stassano et al., "Mid-term results of the valve-on-valve technique for bioprosthetic failure," Eur. J. Cardiothorac. Surg. 2000; 18:453-457.
Pavcnik et al., "Aortic and venous valve for percutaneous insertion," Min. Invas. Ther. & Allied Techol. 2000, vol. 9, pp. 287-292.

* cited by examiner

DELIVERY SYSTEMS AND METHODS OF IMPLANTATION FOR PROSTHETIC HEART VALVES

CROSS-REFERENCE TO RELATED APPLICATION

The present application is a Continuation of U.S. patent application Ser. No. 15/927,841, filed Mar. 21, 2018, which is a Continuation of U.S. patent application Ser. No. 15/183,906, filed Jun. 16, 2016, now U.S. Pat. No. 9,925,079, which is a Continuation of U.S. patent application Ser. No. 12/358,789, filed Jan. 23, 2009, now U.S. Pat. No. 9,393,115, which claims priority to U.S. Provisional Application No. 61/062,207, filed Jan. 24, 2008, the entire contents of each of which are incorporated herein by reference in their entirety.

TECHNICAL FIELD

The present invention relates to prosthetic heart valves. More particularly, it relates to devices, methods, and delivery systems for percutaneously implanting prosthetic heart valves.

BACKGROUND

Diseased or otherwise deficient heart valves can be repaired or replaced using a variety of different types of heart valve surgeries. Typical heart valve surgeries involve an open-heart surgical procedure that is conducted under general anesthesia, during which the heart is stopped while blood flow is controlled by a heart-lung bypass machine. This type of valve surgery is highly invasive and exposes the patient to a number of potentially serious risks, such as infection, stroke, renal failure, and adverse effects associated with use of the heart-lung machine, for example.

Recently, there has been increasing interest in minimally invasive and percutaneous replacement of cardiac valves. Such surgical techniques involve making a very small opening in the skin of the patient into which a valve assembly is inserted in the body and delivered to the heart via a delivery device similar to a catheter. This technique is often preferable to more invasive forms of surgery, such as the open-heart surgical procedure described above. In the context of pulmonary valve replacement, U.S. Patent Application Publication Nos. 2003/0199971 A1 and 2003/0199963 A1, both filed by Tower, et al., describe a valved segment of bovine jugular vein, mounted within an expandable stent, for use as a replacement pulmonary valve. The replacement valve is mounted on a balloon catheter and delivered percutaneously via the vascular system to the location of the failed pulmonary valve and expanded by the balloon to compress the valve leaflets against the right ventricular outflow tract, anchoring and sealing the replacement valve. As described in the articles: "Percutaneous Insertion of the Pulmonary Valve", Bonhoeffer, et al., Journal of the American College of Cardiology 2002; 39: 1664-1669 and "Transcatheter Replacement of a Bovine Valve in Pulmonary Position", Bonhoeffer, et al., Circulation 2000; 102: 813-816, the replacement pulmonary valve may be implanted to replace native pulmonary valves or prosthetic pulmonary valves located in valved conduits.

Various types and configurations of prosthetic heart valves are used in percutaneous valve procedures to replace diseased natural human heart valves. The actual shape and configuration of any particular prosthetic heart valve is dependent to some extent upon the valve being replaced (i.e., mitral valve, tricuspid valve, aortic valve, or pulmonary valve). In general, the prosthetic heart valve designs attempt to replicate the function of the valve being replaced and thus will include valve leaflet-like structures used with either bioprostheses or mechanical heart valve prostheses. In other words, the replacement valves may include a valved vein segment that is mounted in some manner within an expandable stent to make a stented valve. In order to prepare such a valve for percutaneous implantation, the stented valve can be initially provided in an expanded or uncrimped condition, then crimped or compressed around the balloon portion of a catheter until it is as close to the diameter of the catheter as possible.

Other percutaneously-delivered prosthetic heart valves and systems for delivering them have been suggested, such as by Bonhoeffer, P. et al., "Transcatheter Implantation of a Bovine Valve in Pulmonary Position." Circulation, 2002; 102:813-816, and by Cribier, A. et al. "Percutaneous Transcatheter Implantation of an Aortic Valve Prosthesis for Calcific Aortic Stenosis." Circulation, 2002; 106:3006-3008, the disclosures of which are incorporated herein by reference. These heart valves and delivery techniques rely at least partially upon a frictional type of engagement between the expanded support structure and the native tissue to maintain a position of the delivered prosthesis, although the stents can also become at least partially embedded in the surrounding tissue in response to the radial force provided by the stent and balloons that are sometimes used to expand the stent. Thus, with these transcatheter techniques, conventional sewing of the prosthetic heart valve to the patient's native tissue is not necessary. Similarly, in an article by Bonhoeffer, P. et al. titled "Percutaneous Insertion of the Pulmonary Valve." J Am Coll Cardiol, 2002; 39:1664-1669, the disclosure of which is incorporated herein by reference, percutaneous delivery of a biological valve is described. The valve is sutured to an expandable stent within a previously implanted valved or non-valved conduit, or a previously implanted valve. Again, radial expansion of the secondary valve stent is used for placing and maintaining the replacement valve.

Although there have been advances in percutaneous valve replacement techniques and devices, there is a continued desire to provide different delivery systems for delivering cardiac valves to an implantation site in a minimally invasive and percutaneous manner. There is also a continued desire to be able to reposition and/or retract the valves once they have been deployed or partially deployed in order to ensure optimal placement of the valves within the patient. In addition, there is a desire to provide a valve and corresponding delivery system that allow for full or partial repositionability and/or retractability of the valve once it is positioned in the patient.

SUMMARY

The delivery systems of the invention can be used to deliver replacement valves to the heart of a patient. These replacement heart valves may be configured to provide complimentary features that promote optimal placement of the replacement heart valve in a native heart valve, such as the aortic valve, mitral valve, pulmonic valve, and/or tricuspid valve. In some embodiments, the replacement heart valves of the invention are highly amenable to transvascular delivery using an antegrade transapical approach (either with or without cardiopulmonary bypass and either with or without rapid pacing) or retrograde transarterial approach (either with or without rapid pacing). The methodology associated with the present invention can be repeated multiple times, such that several prosthetic heart valves of the present invention can be mounted on top of or within one another, if necessary or desired.

The replacement heart valves each include a stent to which a valve structure is attached. The stents of the invention include a wide variety of structures and features that can be used alone or in combination with features of other stents of the invention. In particular, these stents provide a number of different docking and/or anchoring structures that are conducive to percutaneous delivery thereof. Many of the structures are thus compressible to a relatively small diameter for percutaneous delivery to the heart of the patient, and then are expandable either via removal of external compressive forces (e.g., self-expanding stents). The devices delivered by the delivery systems described herein can be used to deliver stents, valved stents, or other interventional devices such as ASD (atrial septal defect) closure devices, VSD (ventricular septal defect) closure devices, or PFO (patent foramen ovale) occluders.

Methods for insertion of the replacement heart valves of the invention include delivery systems that can maintain the stent structures in their compressed state during their insertion and allow or cause the stent structures to expand once they are in their desired location. In addition, delivery methods of the invention can include features that allow the stents to be retrieved for removal or relocation thereof after they have been deployed or partially deployed from the stent delivery systems. The methods may include implantation of the stent structures using either an antegrade or retrograde approach. Further, in many of the delivery approaches of the invention, the stent structure is rotatable in vivo to allow the stent structure to be positioned in a desired orientation.

BRIEF DESCRIPTION OF THE DRAWINGS

The present invention will be further explained with reference to the appended Figures, wherein like structure is referred to by like numerals throughout the several views, and wherein.

DETAILED DESCRIPTION

Figure 1:
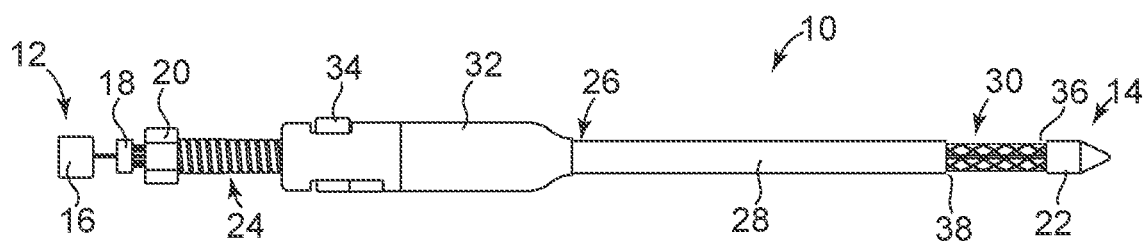
FIG. 1 is a front view of one embodiment of a delivery system of the invention.

As referred to herein, the prosthetic heart valves used in accordance with the various devices and methods may include a wide variety of different configurations, such as a prosthetic heart valve that has tissue leaflets or a synthetic heart valve that has polymeric, metallic, or tissue-engineered leaflets. In this way, the heart valves can be specifically configured for replacing any heart valve. That is, while much of the description herein refers to replacement of aortic valves, the prosthetic heart valves of the invention can also generally be used for replacement of native mitral, pulmonic, or tricuspid valves, for use as a venous valve, or to replace a failed bioprosthesis, such as in the area of an aortic valve or mitral valve, for example.

Although each of the valves used with the delivery devices and methods described herein would typically include leaflets attached within an interior area of a stent, the leaflets are not shown in the illustrated embodiments for clarity purposes. In general, the stents described herein include a support structure comprising a number of strut or wire portions arranged relative to each other to provide a desired compressibility and strength to the heart valve. Other details on particular configurations of the stents of the invention are also described below; however, in general terms, stents of the invention are generally tubular support structures, and leaflets will be secured to the support structure. The leaflets can be formed from a variety of materials, such as autologous tissue, xenograph material, or synthetics as are known in the art. The leaflets may be provided as a homogenous, biological valve structure, such as a porcine, bovine, or equine valve. Alternatively, the leaflets can be provided independent of one another (e.g., bovine or equine pericardial leaflets) and subsequently assembled to the support structure of the stent. In another alternative, the stent and leaflets can be fabricated at the same time, such as may be accomplished using high strength nano-manufactured NiTi films produced at Advanced Bio Prosthetic Surfaces (ABPS) of San Antonio, Texas, for example. The support structures are generally configured to accommodate three leaflets; however, the replacement prosthetic heart valves can incorporate more or less than three leaflets.

In more general terms, the combination of a support structure with one or more leaflets for a replacement heart valve that is delivered by the delivery systems of the invention can assume a variety of other configurations that differ from those shown and described, including any known prosthetic heart valve design. In certain embodiments of the invention, the support structure with leaflets can be any known expandable prosthetic heart valve configuration, whether balloon expandable, self-expanding, or unfurling (as described, for example, in U.S. Pat. Nos. 3,671,979; 4,056,854; 4,994,077; 5,332,402; 5,370,685; 5,397,351; 5,554,185; 5,855,601; and 6,168,614; U.S. Patent Application Publication No. 2004/0034411; Bonhoeffer P., et al., "Percutaneous Insertion of the Pulmonary Valve", Pediatric Cardiology, 2002; 39:1664-1669; Anderson H R, et al., "Transluminal Implantation of Artificial Heart Valves", EUR Heart J., 1992; 13:704-708; Anderson, J. R., et al., "Transluminal Catheter Implantation of New Expandable Artificial Cardiac Valve", EUR Heart J., 1990, 11: (Suppl) 224a; Hilbert S. L., "Evaluation of Explanted Polyurethane Trileaflet Cardiac Valve Prosthesis", J Thorac Cardiovascular Surgery, 1989; 94:419-29; Block P C, "Clinical and Hemodyamic Follow-Up After Percutaneous Aortic Valvuloplasty in the Elderly", The American Journal of Cardiology, Vol. 62, Oct. 1, 1998; Boudjemline, Y., "Steps Toward Percutaneous Aortic Valve Replacement", Circulation, 2002; 105:775-558; Bonhoeffer, P., "Transcatheter Implantation of a Bovine Valve in Pulmonary Position, a Lamb Study", Circulation, 2000:102:813-816; Boudjemline, Y., "Percutaneous Implantation of a Valve in the Descending Aorta In Lambs", EUR Heart J, 2002; 23:1045-1049; Kulkinski, D., "Future Horizons in Surgical Aortic Valve Replacement: Lessons Learned During the Early Stages of Developing a Transluminal Implantation Technique", ASAIO J, 2004; 50:364-68; the teachings of which are all incorporated herein by reference).

Orientation and positioning of the stents of the invention may be accomplished either by self-orientation of the stents (such as by interference between features of the stent and a previously implanted stent or valve structure) or by manual orientation of the stent to align its features with anatomical or previous bioprosthetic features, such as can be accomplished using fluoroscopic visualization techniques, for example. For example, when aligning the stents of the invention with native anatomical structures, they should be aligned so as to not block the coronary arteries, and native mitral or tricuspid valves should be aligned relative to the anterior leaflet and/or the trigones/commissures.

Some embodiments of the support structures of the stents described herein can be a series of wires or wire segments arranged so that they are capable of transitioning from a collapsed state to an expanded state. The stents may further include a number of individual wires formed of a metal or other material. These wires are arranged in such a way that a support structure allows for folding or compressing to a contracted state in which its internal diameter is greatly reduced from its internal diameter in an expanded state. The delivery systems used for such a stent should be provided with degrees of rotational and axial orientation capabilities in order to properly position the new stent at its desired location.

The wires of the support structure of the stents can be formed from a shape memory material such as a nickel titanium alloy (e.g., Nitinol). With this material, the support structure is self-expandable from a contracted state to an expanded state, such as by the application of heat, energy, and the like, or by the removal of external forces (e.g., compressive forces). This support structure can also be repeatedly compressed and re-expanded multiple times without damaging the structure of the stent. In addition, the support structure of such an embodiment may be laser cut from a single piece of material or may be assembled from a number of different components. For these types of stent structures, one example of a delivery system that can be used includes a catheter with a retractable sheath that covers the stent until it is to be deployed, at which point the sheath can be retracted to allow the stent to expand. Further details of such embodiments are discussed below.

Referring now to the Figures, wherein the components are labeled with like numerals throughout the several Figures, and initially to FIG. 1, one embodiment of a stent delivery system 10 is illustrated. This system 10 includes a proximal end 12 and a distal end 14. Proximal end 12 includes a tip knob 16, a hook driver 18, and a stop 20, all of which are used in controlling the delivery and deployment of a stent 30 at the generally distal end 14 of the delivery system 10. The distal end 14 of the delivery system 10 includes a tip 22, which is shown adjacent to the stent 30. The delivery system further includes a threaded rod 24 and a sheath 26. The sheath 26 generally includes an elongated tubular portion 28 that has a hollow interior portion with a first diameter that is sized for compression and retention of the stent 30 within its interior area prior to deployment of the stent 30.

The sheath 26 further includes a handle portion 32 that is proximal to the elongated portion 28. The handle portion 32 is designed to be held and manipulated by the user for controlling the longitudinal movement of the sheath 26. The handle portion 32 further includes an internal threaded mechanism that engages with the threaded rod 24 to provide incremental linear movement of the sheath 26 along the length of the delivery system 10. That is, the sheath 26 is moveable toward either the proximal end 12 or distal end 14 by rotating the handle portion 32 about the longitudinal axis of the delivery system, thereby moving the inner threaded mechanism along the helical screw of the threaded rod 24. The sheath 26 may or may not rotate with the handle portion 32. The handle portion 32 further includes a push-button 34 that releases the inner threaded portion of the sheath from its engagement with the threaded rod 24 so that the sheath 26 can slide relatively freely along the length of the threaded rod 24. Thus, the sheath 26 also has the capability of being quickly advanced or retracted when its inner threaded mechanism is released from the threaded rod 24, while also having the capability of being advanced and retracted more slowly and accurately by rotating the handle portion 32 along the threaded rod 24.

The exemplary stent 30 is made of a series of wires that are compressible and expandable through the application and removal of external forces, and may include a series of Nitinol wires that are approximately 0.010-0.015 inches in cross-section. That is, the stent 30 in this embodiment is a self-expanding stent. As shown in FIG. 1, the stent 30 is captured at a first end 36 by the tip 22 and is captured at a second end 38 by the sheath 26. This configuration of the delivery system 10 enables independent release of the first and second ends 36, 38 of the stent of the stent 30 from the system. In this way, both ends of the stent 30 can be controlled during the deployment thereof to be sure that it is properly positioned within the target anatomy prior to fully releasing the stent 30 from the delivery system 10. The mechanical stop 20 is located at the proximal end of the threaded rod 24 to control the distance that the sheath 26 can be moved toward the proximal end 12 during the process of unsheathing the stent 30.

Another exemplary delivery system 100 and process of deploying a stent 130 is illustrated in FIGS. 2-10. This method can be used for apical delivery of a stent to an aorta, or it can be used for other delivery approaches, such as for transarterial retrograde delivery. The delivery system 100 provides the capability for loading of a stent 130 onto the system, at least partially deploying the stent, then retracting the stent back into the delivery system and relocating it, if desired.

Figure 2:
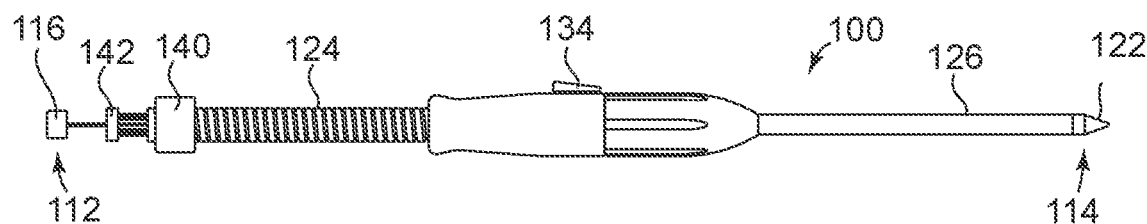
FIG. 2 is a front view of another embodiment of a delivery system of the invention with its sheath in a closed position.

In particular, FIG. 2 illustrates a delivery system 100 including a distal tip 122 adjacent to a sheath 126 in which a stent is enclosed. The stent 130 of this embodiment is illustrated as being engaged with multiple wires or elements having angled end portions or protrusions, although it is understood that the stent could be attached to the delivery system using an alternate attachment configuration. In the embodiment of FIG. 2 and as is more clearly shown in the enlarged view of FIG. 6, the delivery system includes multiple elements 150 extending from the distal end of the sheath 126. The number of elements 150 is preferably the same as the number of crowns at a proximal end 136 of the stent 130, although the number of elements 150 can be different from the number of crowns. Each of the elements 150 includes an angled wire tip or protrusion 152 that extends at an angle from its respective element 150. The angle between the protrusion or tip 152 and its respective element 150 can be approximately 90 degrees, although it can be any angle that provides for secure engagement between the elements 150 and the stent 130 in the manner described below. Alternatively, a suture or wire without an angled tip or protrusion 152 could be used to securely engage the stent to the delivery system 100, or an attachment end could contain multiple protrusions that fit to the stent. In another alternative, the stent itself can include a structure for engagement with a delivery system. In any case, it is important that the geometry of the stent and/or any type of stent engaging elements provide for both secure capture of the stent and easy stent release from the delivery system, when desired.

Figure 6:
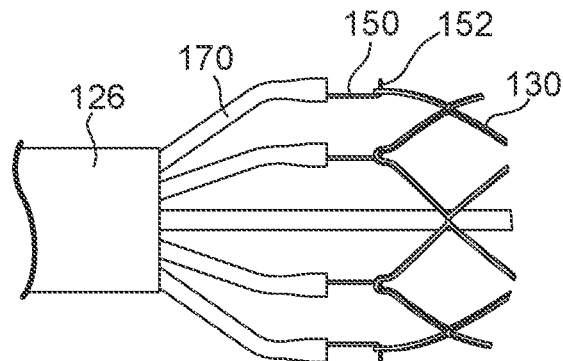
FIG. 6 is an enlarged front view of a portion of the delivery system and stent of FIG. 5.

Referring specifically to FIG. 6, the elements 150 with an angled wire tip or protrusion 152 are shown in an enlarged view. In this configuration, a sleeve 170 is positioned over the relatively straight portion of wire or element 150, but retracted relative to its angled wire tip 152. When the element 150 is engaged with the stent crown, the sleeve 170 can be slid toward the stent crown until it encases both the end of the stent crown and the angled wire tip or protrusion 152, thereby providing a more secure attachment of the components relative to each other. The sleeve 170 is preferably made of a relatively flexible material that can deform and expand as it slides over the stent crown and angled wire tip 152. This sleeve 170 helps to prevent disengagement of each angled wire tip 152 from its respective stent crown.

The delivery system 100 further includes driver mechanisms at its proximal end 112, including a sheath push-button 134, a counter-rotation knob 140, a hook driver 142, and a tip thumb knob 116. A threaded rod 124 is positioned between the counter-rotation knob 140 and the sheath push-button 134 when the delivery system is at this step of the process. The delivery system 100 can then be used to position the stent 130 in its target location in the patient.

Figure 3:
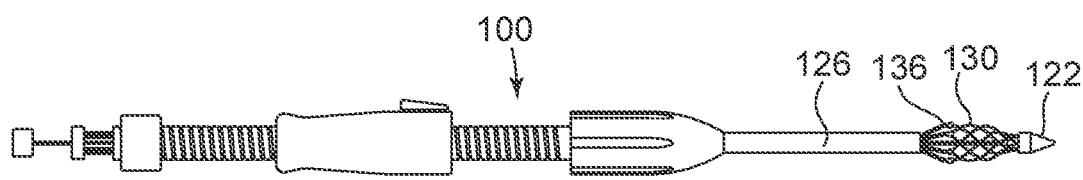
FIG. 3 is a front view of the delivery system of FIG. 2, with its sheath partially retracted to expose and partially expand a stent.

For an antegrade approach (e.g., a transapical approach), once the delivery system 100 has been located within the patient so that the stent and/or valve is in its desired position, such as within the aortic valve, the sheath 126 is pulled back toward the proximal end 112 of the delivery system, as shown in FIG. 3, until it exposes the inflow (proximal) end of the stent 130. This removal of the compressive force provided by the sheath allows the stent 130 to then expand radially. Alternatively, in a transarterial retrograde delivery approach, the inflow or distal end of the stent 130 can remain compressed while the middle, or middle and proximal end, of the stent, along with other features such as petals, for example, are radially expanded. Any minor positional adjustments, if necessary, can be made at this point. However, if it is determined that the stent 130 is far enough from the desired position that major repositioning is necessary, the sheath 126 can be moved back toward the distal end 114 of the delivery system 100 until the entire stent 130 is again enclosed within the sheath 126. The delivery system 100 can then be repositioned until it is in its desired location. The delivery system 100 may also include a stop on its handle or some other portion of its structure that requires a positive action by the user to prevent inadvertent release of the stent 130 from the delivery system 100.

Figure 4:
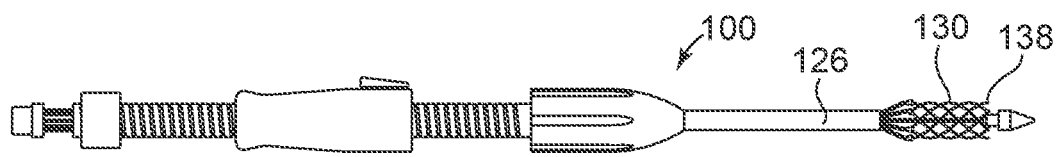
FIG. 4 is a front view of the delivery system of FIG. 3, with a distal end of the stent released from a distal tip of the delivery system.

FIG. 4 illustrates the step of deploying the outflow (distal) end of the stent 130. In this step, the tip thumb knob 116 near the proximal end 112 is pressed to deploy the outflow end of the stent 130 so that it is free from the distal tip portion 122. When using an alternative transarterial retrograde approach, this mechanism can instead be used to radially expand the inflow end of the stent 130 after the middle portion of the stent 130, along with any other features provided on the stent such as petals, are radially expanded.

Figure 5:
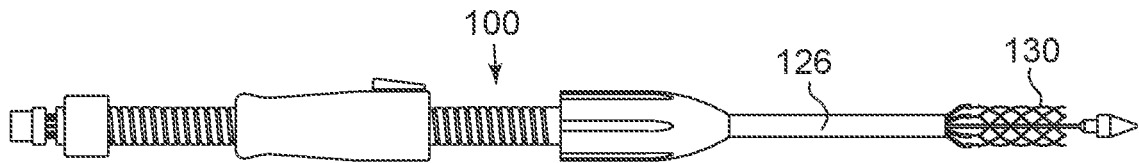
FIG. 5 is a front view of the delivery system of FIG. 4 with its hook driver in a stent-releasing position.
Figure 7:
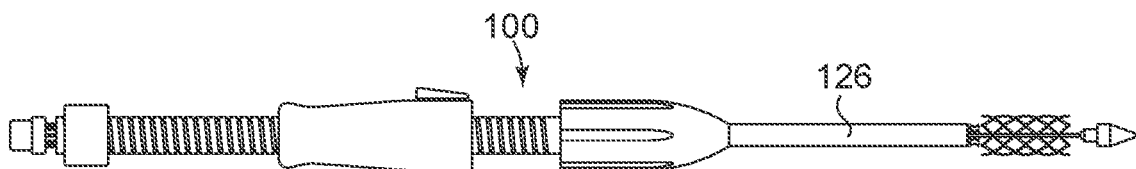
FIG. 7 is a front view of the delivery system of FIG. 5, with the stent released or deployed from the delivery system.
Figure 8:
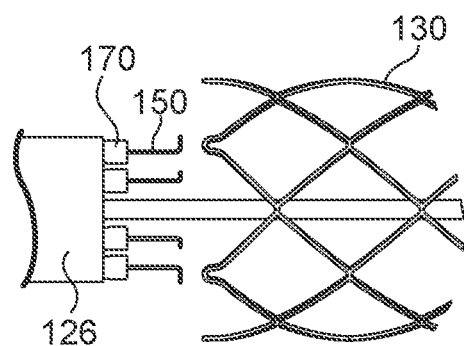
FIG. 8 is an enlarged front view of a portion of the delivery system and deployed stent of FIG. 7.
Figure 9:
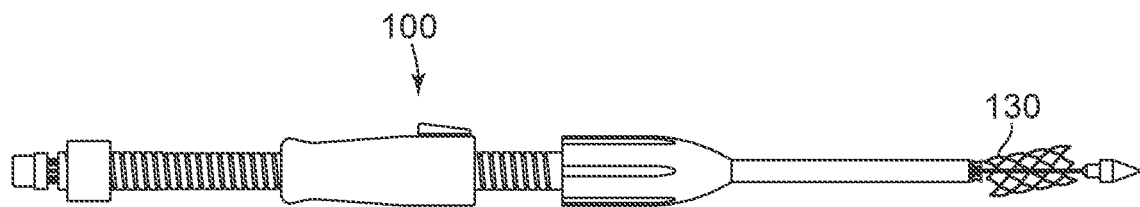
FIG. 9 is another front view of the delivery system of FIG. 7.

As shown in FIGS. 5 and 6, the hook driver 142 can be translated distally to release the stent 130 from the sleeves 170 that covered the angled wire tips 152 and their corresponding stent crowns. This is accomplished by driving the hooks or angled wire tips 152 forward. The sheath 126 is then driven toward the stent 130 to move the wire tips 152 toward the central axis of the delivery system 100 and toward the central axis of the stent 130, thereby allowing the inflow (proximal) end of the stent 130 to fully release from delivery system 100, as shown in FIGS. 7-9.

In an alternative embodiment, in order to deploy a stent when it is properly positioned in a lumen of the patient, the sheath can be pulled back to expose the stent and the wires engaged with the crowns of the stent. The stent can be released by pulling the wires back toward the central axis of the device to disengage them from the stent crowns. The process of pulling the wires toward the central axis can be accomplished in a number of ways, such as by rotating the sheath over coarse threads or pushing a sheath push-button to slide it to pull the wires toward the central axis and away from the stent. However, a number of different mechanisms can be used to accomplish this movement of the wires relative to the stent crowns. One example of an alternative mechanism for releasing the stent from the delivery system is to pull sleeves back from their respective angled wire tips or protrusions.

Figure 10:
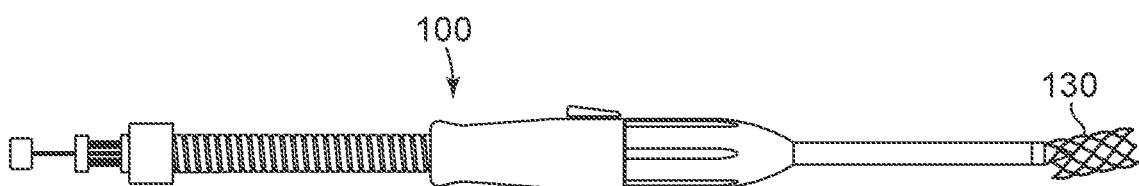
FIG. 10 is a front view of the delivery system of FIG. 9, with the sheath positioned at the distal end of the system and enclosing the tips of the wires that had been engaged with the stent.

The hook driver 142 is then translated proximally to pull the angled wire tips 152 of the wires 150 into the same sleeves 170 that are also used to secure the angled wire tips 152 to the stent crowns. In this way, the angled wire tips 152 are protected from getting caught on the sheath 126 when the sheath 126 is driven toward the outflow end of the delivery system 100 to cover or "re-sheath" the wires 150 prior to removing the system 100 from the patient, as shown in FIG. 10. If the stent 130 includes crowns that are not all generally in the same plane (e.g., some crowns are further from one of the ends of the stent than other crowns), the delivery system 100 may include wires that have different lengths in order to capture all of the stent crowns. Thus, the delivery system provides both the function of withdrawing the sheath 126 and withdrawing the sleeves 170, when desired in the stent delivery process.

It is noted that in the above procedure, the stent can be retracted back into the sheath at any point in the process until the wires are disengaged from the stent. This may be useful for repositioning of the stent if it is determined that the stent has been improperly positioned relative to the patient's anatomy. In this case, the steps described above can be repeated until the desired positioning of the stent in the patient's anatomy is achieved.

With this system described above, full or partial blood flow through the valve can advantageously be maintained during the period when the stented valve is being deployed into the patient but is not yet released from its delivery system. This feature can help to prevent complications that may occur when blood flow is stopped or blocked during valve implantation with some other known delivery systems. In addition, it is possible for the clinician to thereby evaluate the opening and closing of leaflets, examine for any paravalvular leakage and evaluate coronary flow and proper positioning of the valve within the target anatomy before final release of the stented valve.

The delivery systems described above can be modified to additionally or alternatively deliver a balloon-expandable stent to the target site of the patient. Delivering balloon-expandable stents to the implantation location can be performed percutaneously. In general terms, this includes providing a transcatheter assembly, including a delivery catheter, a balloon catheter, and a guide wire. Some delivery catheters of this type are known in the art, and define a lumen within which the balloon catheter is received. The balloon catheter, in turn, defines a lumen within which the guide wire is slideably disposed. Further, the balloon catheter includes a balloon that is fluidly connected to an inflation source. For a balloon-expandable stent, the transcatheter assembly is appropriately sized for a desired percutaneous approach to the implantation location. For example, the transcatheter assembly can be sized for delivery to the heart valve via an opening at a carotid artery, a jugular vein, a sub-clavian artery or vein, femoral artery or vein, or the like. Essentially, any percutaneous intercostal or vascular penetration can be made to facilitate use of the transcatheter assembly.

Prior to delivery, the stent is mounted over the balloon in a contracted state to be as small as possible without causing permanent deformation of the stent structure. As compared to the expanded state, the support structure is compressed onto itself and the balloon, thus defining a decreased inner diameter as compared to an inner diameter in the expanded state. While this description is related to the delivery of a balloon-expandable stent, the same basic procedures can also be applicable to a self-expanding stent, where the delivery system would not include a balloon, but would preferably include a sheath or some other type of configuration for maintaining the stent in a compressed condition until its deployment.

With the stent mounted to the balloon, the transcatheter assembly is delivered through a percutaneous opening (not shown) in the patient via the delivery catheter. The implantation location is located by inserting the guide wire into the patient, which guide wire extends from a distal end of the delivery catheter, with the balloon catheter otherwise retracted within the delivery catheter. The balloon catheter is then advanced distally from the delivery catheter along the guide wire, with the balloon and stent positioned relative to the implantation location. In an alternative embodiment, the stent is delivered to an implantation location via a minimally invasive surgical incision (i.e., non-percutaneously). In another alternative embodiment, the stent is delivered via open heart/chest surgery. In one embodiment of the stents of the invention, the stent includes a radiopaque, echogenic, or Mill visible material to facilitate visual confirmation of proper placement of the stent. Alternatively, other known surgical visual aids can be incorporated into the stent. The techniques described relative to placement of the stent within the heart can be used both to monitor and correct the placement of the stent in a longitudinal direction relative to the length of the anatomical structure in which it is positioned.

Once the stent is properly positioned, the balloon catheter is operated to inflate the balloon, thus transitioning the stent to an expanded state. Alternatively, where the support structure is formed of a shape memory material, the stent can self-expand to its expanded state.

One or more markers on the valve, along with a corresponding imaging system (e.g., echo, MRI, etc.) can be used with the various repositionable delivery systems described herein in order to verify the proper placement of the valve prior to releasing it from the delivery system. A number of factors can be considered, alone or in combination, to verify that the valve is properly placed in an implantation site, where some exemplary factors are as follows: (1) lack of paravalvular leakage around the replacement valve, which can be advantageously examined while blood is flowing through the valve since these delivery systems allow for flow through and around the valve; (2) optimal rotational orientation of the replacement valve relative to the coronary arteries; (3) the presence of coronary flow with the replacement valve in place; (4) correct longitudinal alignment of the replacement valve annulus with respect to the native patient anatomy; (5) verification that the position of the sinus region of the replacement valve does not interfere with native coronary flow; (6) verification that the sealing skirt is aligned with anatomical features to minimize paravalvular leakage; (7) verification that the replacement valve does not induce arrhythmias prior to final release; and (8) verification that the replacement valve does not interfere with function of an adjacent valve, such as the mitral valve.

The present invention has now been described with reference to several embodiments thereof. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein.

What is claimed is:

1. A method for deploying a stented heart valve, the method comprising:
advancing a delivery system to a desired location, the delivery system including the stented heart valve disposed within a sheath of the delivery system, wherein the stented heart valve includes a first end and a second end, the second end being compressed and retained within a distal tip of the delivery system;
retracting the sheath of the delivery system proximally past the first end of the stented heart valve, wherein the first end of the stented heart valve is retained by the delivery system with the sheath retracting proximal of the first end of the stented heart valve;
advancing the distal tip of the delivery system to release the second end of the stented heart valve; and
releasing the first end of the stented heart valve from the delivery system,
wherein the first end of the stented heart valve is retained by the delivery system by a plurality of elongated stent engagement elements, wherein each stent engagement element includes a stent engagement portion engaged with a crown of a stent at the first end of the stented heart valve, wherein the stent engagement elements and the crowns are equal in quantity, and
wherein the step of releasing the first end of the stented heart valve from the delivery system includes disengaging the stent engagement portion of each stent engagement element from the crown of the stent.

2. The method of claim 1,
wherein the stent engagement portion of each stent engagement element comprises an angled wire tip, and
wherein the step of releasing the first end of the stented heart valve from the delivery system includes disengaging the angled wire tip of each stent engagement element from the stent.

3. The method of claim 1,
wherein the delivery system further includes plurality of elongated sleeves, wherein each elongated sleeve surrounds a respective one of the stent engagement portions and a portion of the stent of the stented heart valve to engage the stent engagement portion with the stent, and
wherein the step of releasing the first end of the stented heart valve from the delivery system comprises proximally retracting the elongated sleeves such that each elongated sleeve is spaced proximally of the respective stent engagement portion.

4. The method of claim 3, wherein the step of releasing the first end of the stented heart valve from the delivery device further comprises, after proximally retracting the elongated sleeves, distally advancing the sheath to cause the stent engagement portions to move towards a central longitudinal axis of the delivery system to disengage the stent engagement portions from the stent.

5. The method of claim 4, wherein the sheath is proximally retracted proximal of the first end of the stented heart valve, then the distal tip is advanced to release the second end of the stented heart valve, then the plurality of elongated sleeves are proximally retracted and the sheath is distally advanced to release the first end of the stented heart valve.

6. The method of claim 3, wherein after the stented heart valve is released from the delivery system, the method further comprises advancing the elongated sleeves to cover the stent engagement portions.

7. A method for deploying a stented heart valve, the method comprising:
advancing a delivery system including the stented heart valve disposed therein to a desired location;
retracting a sheath of the delivery system proximally past a first end of the stented heart valve, wherein the first end the stented heart valve is retained by the delivery system with the sheath retracting proximal of the first end of the stented heart valve by a plurality of elongated stent engagement elements, wherein each stent engagement element includes a stent engagement portion engaged with a stent of the stented heart valve; and
releasing the first end of the stented heart valve from the delivery system by disengaging the stent engagement portion of each stent engagement element from the stent,
wherein the stented heart valve is radially expanded to a fully deployed configuration via self-expansion or balloon-expansion,
wherein the stent engagement portion of each stent engagement element comprises an angled wire tip, and
wherein the step of releasing the first end of the stented heart valve from the delivery system includes disengaging the angled wire tip of each stent engagement element from the stent.

8. The method of claim 7,
wherein the delivery system further includes a plurality of elongated sleeves such that when the stent engagement portions of the elongated stent engagement elements are engaged with the stent, each elongated sleeve surrounds a respective one of the stent engagement portions and a portion of a stent of the stented heart valve to engage the stent engagement portion with the stent, and
wherein the step of releasing the first end of the stented heart valve from the delivery system comprises proximally retracting the elongated sleeves such that each elongated sleeve is spaced proximally of the respective stent engagement portion.

9. The method of claim 8, wherein the step of releasing the first end of the stented heart valve from the delivery device further comprises, after proximally retracting the elongated sleeves, distally advancing the sheath to cause the stent engagement portions to move towards a central longitudinal axis of the delivery system to disengage the stent engagement portions from the stent.

10. The method of claim 9, wherein after the stented heart valve is released from the delivery system, the method further comprises advancing the elongated sleeves to cover the stent engagement portions.

11. The method of claim 7, wherein during the advancing the delivery system step a second end of the stented heart valve is compressed and retained within a distal tip of the delivery system, and wherein proximal retraction of the sheath does not release the second end of the stented heart valve from the distal tip, the method further comprising advancing the distal tip distally to release the second end of the stented heart valve.

12. The method of claim 11, wherein the second end of the stented heart valve is released prior to releasing the first end of the stented heart valve.

13. The method of claim 7, wherein the stented heart valve is radially expanded to the fully deployed configuration via self-expansion.

14. The method of claim 7, wherein the stented heart valve is radially expanded to the fully deployed configuration via balloon-expansion.

15. A method for deploying a stented heart valve, the method comprising:
advancing a delivery system including the stented heart valve disposed therein to a desired location;
retracting a sheath of the delivery system proximally past a first end of the stented heart valve, wherein the first end the stented heart valve is retained by the delivery system with the sheath retracting proximal of the first end of the stented heart valve by a plurality of elongated stent engagement elements, wherein each stent engagement element includes a stent engagement portion engaged with a stent of the stented heart valve; and
releasing the first end of the stented heart valve from the delivery system by disengaging the stent engagement portion of each stent engagement element from the stent,
wherein the stented heart valve is radially expanded to a fully deployed configuration via self-expansion or balloon-expansion,
wherein the delivery system further includes a plurality of elongated sleeves such that when the stent engagement portions of the elongated stent engagement elements are engaged with the stent, each elongated sleeve surrounds a respective one of the stent engagement portions and a portion of a stent of the stented heart valve to engage the stent engagement portion with the stent, and
wherein the step of releasing the first end of the stented heart valve from the delivery system comprises proximally retracting the elongated sleeves such that each elongated sleeve is spaced proximally of the respective stent engagement portion.

16. The method of claim 15, wherein the step of releasing the first end of the stented heart valve from the delivery device further comprises, after proximally retracting the elongated sleeves, distally advancing the sheath to cause the stent engagement portions to move towards a central longitudinal axis of the delivery system to disengage the stent engagement portions from the stent.

17. The method of claim 16, wherein the stent engagement portion of each of the plurality of elongated stent engagement elements comprises an angled wire tip, and wherein the step of releasing the first end of the stented heart valve from the delivery device comprises disengaging the angled wire tip from the stent.

18. The method of claim 17, wherein after the stented heart valve is released from the delivery system, the method further comprises advancing the elongated sleeves to cover the stent engagement portions.

19. The method of claim 15, wherein during the advancing the delivery system step a second end of the stented heart valve is compressed and retained within a distal tip of the delivery system, and wherein proximal retraction of the sheath does not release the second end of the stented heart valve from the distal tip, the method further comprising advancing the distal tip distally to release the second end of the stented heart valve.

20. The method of claim 19, wherein the second end of the stented heart valve is released prior to releasing the first end of the stented heart valve.

21. The method of claim 15, wherein the stented heart valve is radially expanded to the fully deployed configuration via self-expansion.

22. The method of claim 15, wherein the stented heart valve is radially expanded to the fully deployed configuration via balloon-expansion.

\* \* \* \* \*